(12) United States Patent
Lopez Lastra et al.

(10) Patent No.: US 6,783,977 B1
(45) Date of Patent: Aug. 31, 2004

(54) INTERNAL RIBOSOME ENTRY SITE AND VECTOR CONTAINING SAME

(75) Inventors: Marcelo Lopez Lastra, Lyons (FR); Caroline Gabus-Darlix, Chaponost (FR); Jean-Luc Darlix, Chaponost (FR)

(73) Assignee: Institut National de la Sante et de la Recherche Medicale (INSERM), Paris (FR)

(*) Notice: Subject to any disclaimer, the term of this patent is extended or adjusted under 35 U.S.C. 154(b) by 0 days.

(21) Appl. No.: 09/214,124

(22) PCT Filed: Apr. 28, 1998

(86) PCT No.: PCT/FR98/00849

§ 371 (c)(1),
(2), (4) Date: Mar. 17, 1999

(87) PCT Pub. No.: WO98/49334

PCT Pub. Date: Nov. 5, 1998

(30) Foreign Application Priority Data

Apr. 28, 1997 (FR) ............................................. 97 05203

(51) Int. Cl.[7] .......................... C12P 21/06; C12N 15/63; C07H 21/04
(52) U.S. Cl. .................. 435/320.1; 435/69.1; 435/455; 536/23.1; 536/24.1
(58) Field of Search ........................ 424/93.21; 514/44, 514/2; 435/320.1, 455, 466, 69.1; 536/23.1, 24.1

(56) References Cited

U.S. PATENT DOCUMENTS

| | | | |
|---|---|---|---|
| 5,112,767 A | | 5/1992 | Roy-Burman et al. |
| 5,925,565 A | * | 7/1999 | Berlioz et al. ............... 435/325 |
| 5,997,856 A | * | 12/1999 | Hora et al. ................ 424/85.2 |
| 6,060,273 A | * | 5/2000 | Dirks et al. ................ 435/69.1 |
| 6,136,566 A | * | 10/2000 | Sands et al. ............... 435/69.7 |

FOREIGN PATENT DOCUMENTS

| | | |
|---|---|---|
| WO | 93/03143 | 2/1993 |
| WO | 93/05815 | 4/1993 |
| WO | 94/05785 | 3/1994 |
| WO | 94/05786 | 3/1994 |
| WO | WO 94/29437 | * 12/1994 |
| WO | 96/01324 | 1/1996 |
| WO | 96/15813 | 5/1996 |

OTHER PUBLICATIONS

Ngo et. al.; Computational Complexity, Protein Structure Prediction, and the Levinthal Paradox, 1994, The Protein Folding Problem and Tertiary Structure Prediction:M 491–495.*
Rudinger; Characteristics of the amino acids as components of a peptide hormone sequence, 1976, Peptide Hormones:1–7.*
Dang et al. Clin. Cancer Res. 5:471–474, 1999.*
Wivel, N.A. & Wilson, J.M. Hematol. Oncol. Clin. North Am. 12:483–501, 1998.*
Miller, N. & Vile, R. FASEB J. 9:190–199, 1995.*
Deonarain, M.P. Exp. Opin. Ther. Patents 8:53–69, 1998.*
Verma, I.M. & Somia, N. Nature 389:239–242, 1997.*
Gerson, S.L. Natur Med. 5:262–264, 1999.*
Mullins, L.J. & Mullins, J.J. J. Clin. Invest. 98:S37–S40, 1996.*
Seamark, R.F. Reprod. Fert Dev. 6:653–657, 1994.*
Wall, R.J. Theriogenology 45:57–68, 1996.*
Eck, S.L. & Wilson, J.M. Gene–based therapy. In Goodman & Gilman's The pharmacological basis of therapeutics, Ninth edition, pp. 77–101, 1996.*
Berlioz et al. J. Virol. 69:6400–6407, 1995.*
Lopez–Lastra et al. Hum. gene ther. 8:1855–1865, 1997.*

* cited by examiner

*Primary Examiner*—David Guzo
*Assistant Examiner*—Quang Nguyen
(74) *Attorney, Agent, or Firm*—Burns, Doane, Swecker & Mathis, L.L.P.

(57) ABSTRACT

The invention concerns the use of a nucleotide sequence derived from all or part of the genomic RNA 5' end of a type C retrovirus except for Friend murine leukaemia virus (FMLV) and Moloney murine leukaemia virus (MoMLV) as internal ribosome entry site or as element enabling or improving retrovirus vector packaging. The invention also concerns a vector comprising said nucleotide sequence, a viral particle generated from this vector, a cell comprising this vector or infected by the viral particle, their therapeutic use and a pharmaceutical composition containing them. The invention further concerns the use of a vector, a viral particle or a pharmaceutical composition for transfecting or infecting pluripotent stem cells.

22 Claims, 5 Drawing Sheets

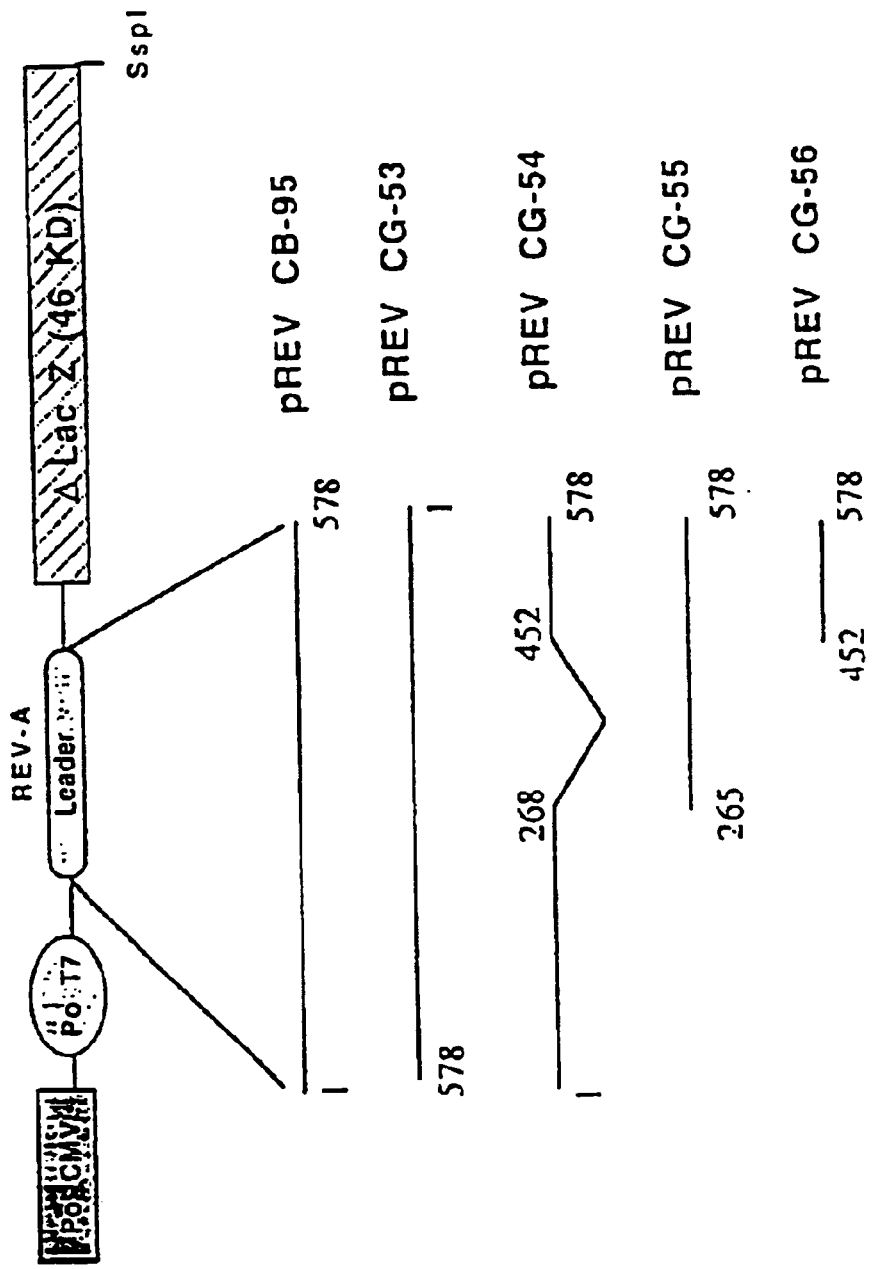
- Figure 1 -

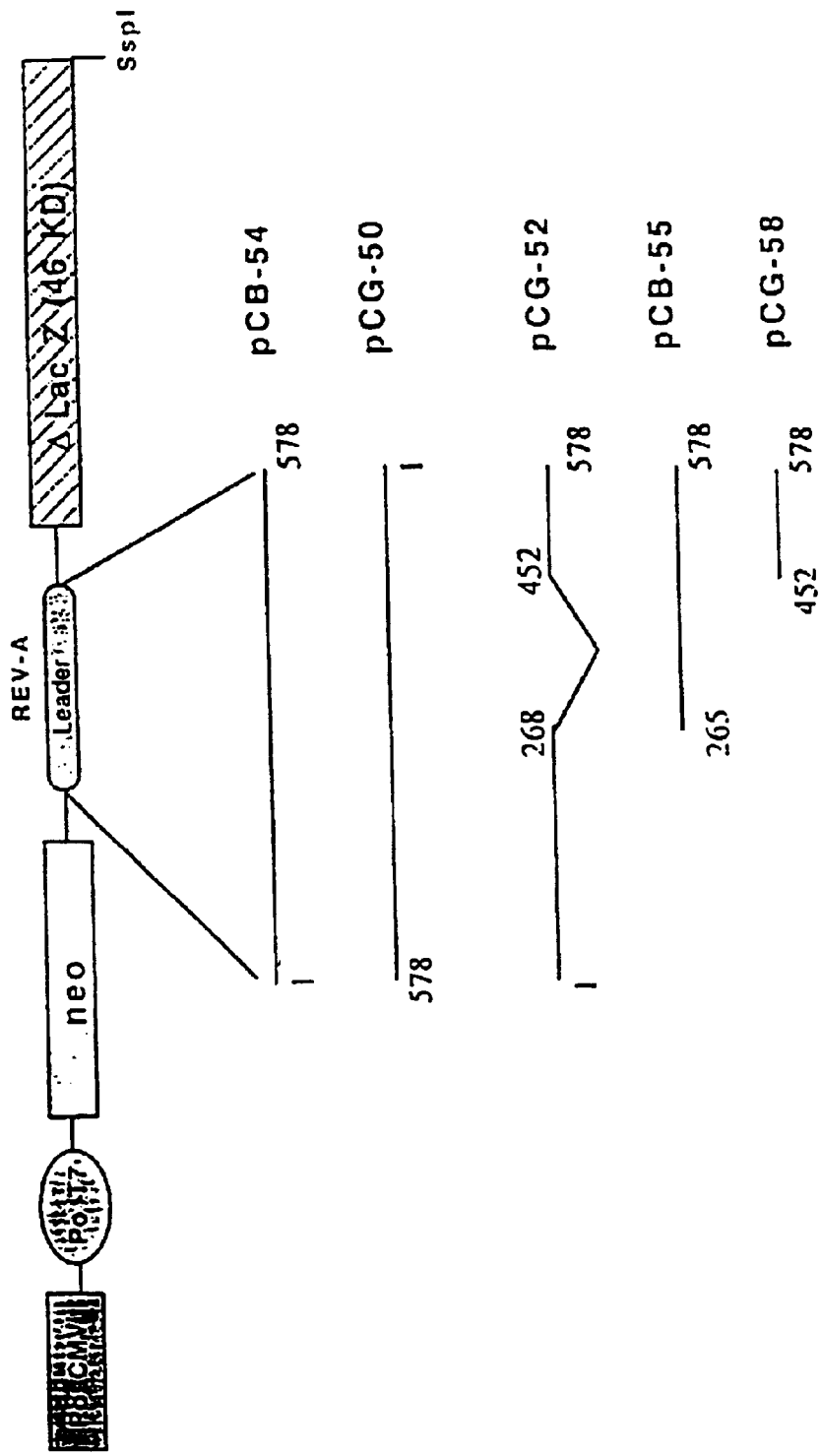
- Figure 2 -

A) General structure of the retroviral vectors
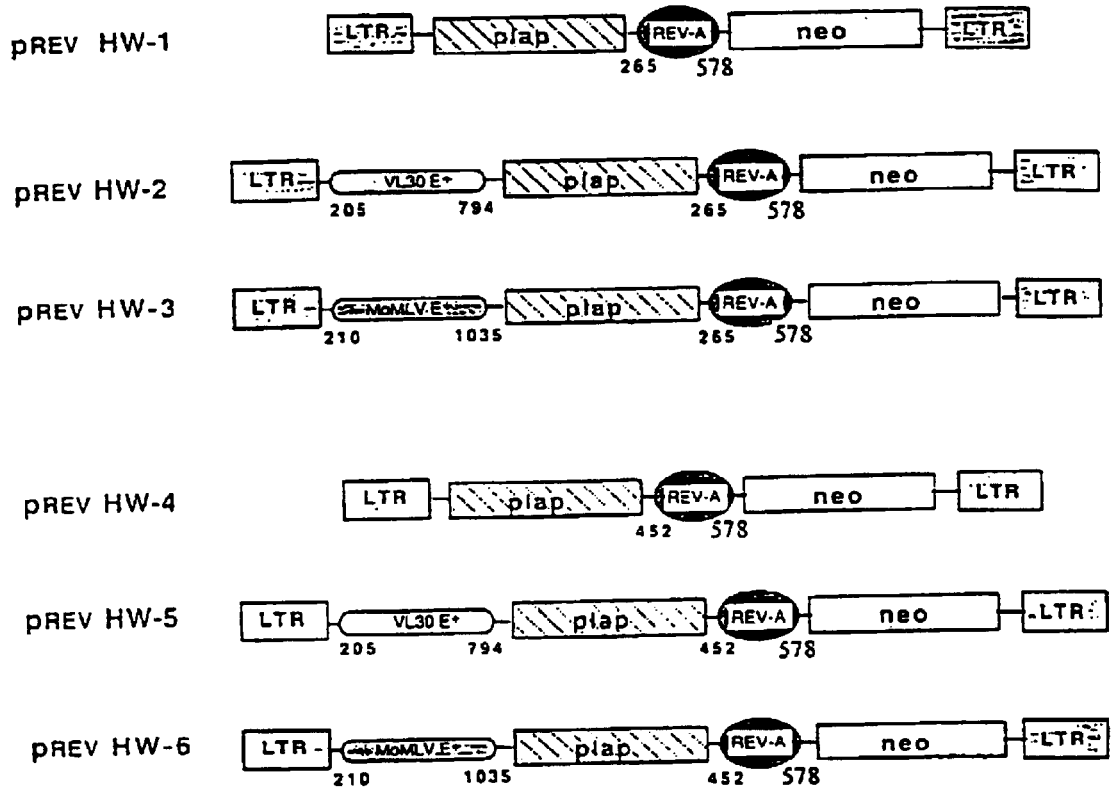
B) New dicistronic retroviral vectors
C) Control vector
- Figure 3 -

A) Effect of ripamycin on the alkaline phosphatase activity
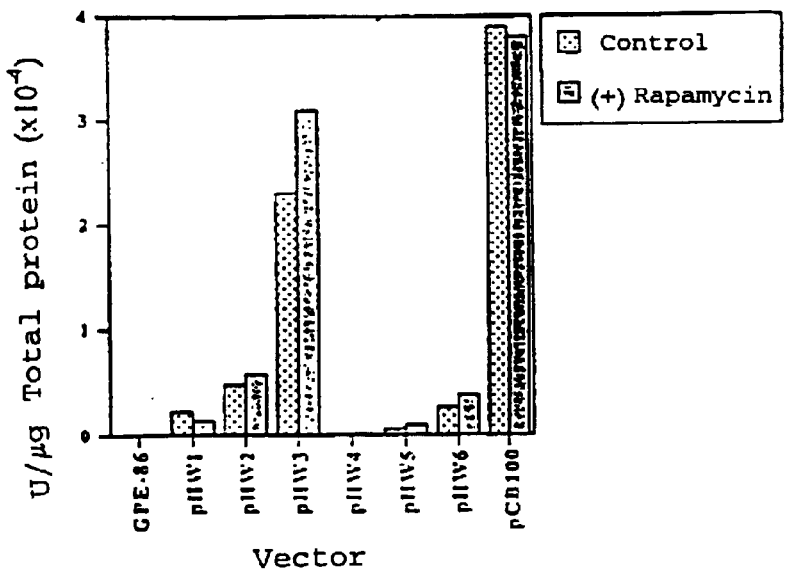
B) Effect of ripamycin on the neomycin phosphotransferase activity
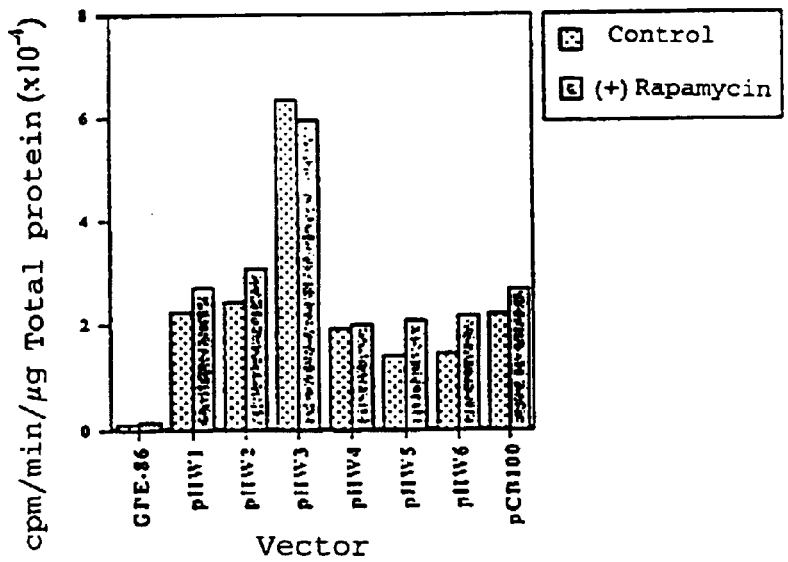
- Figure 4 -

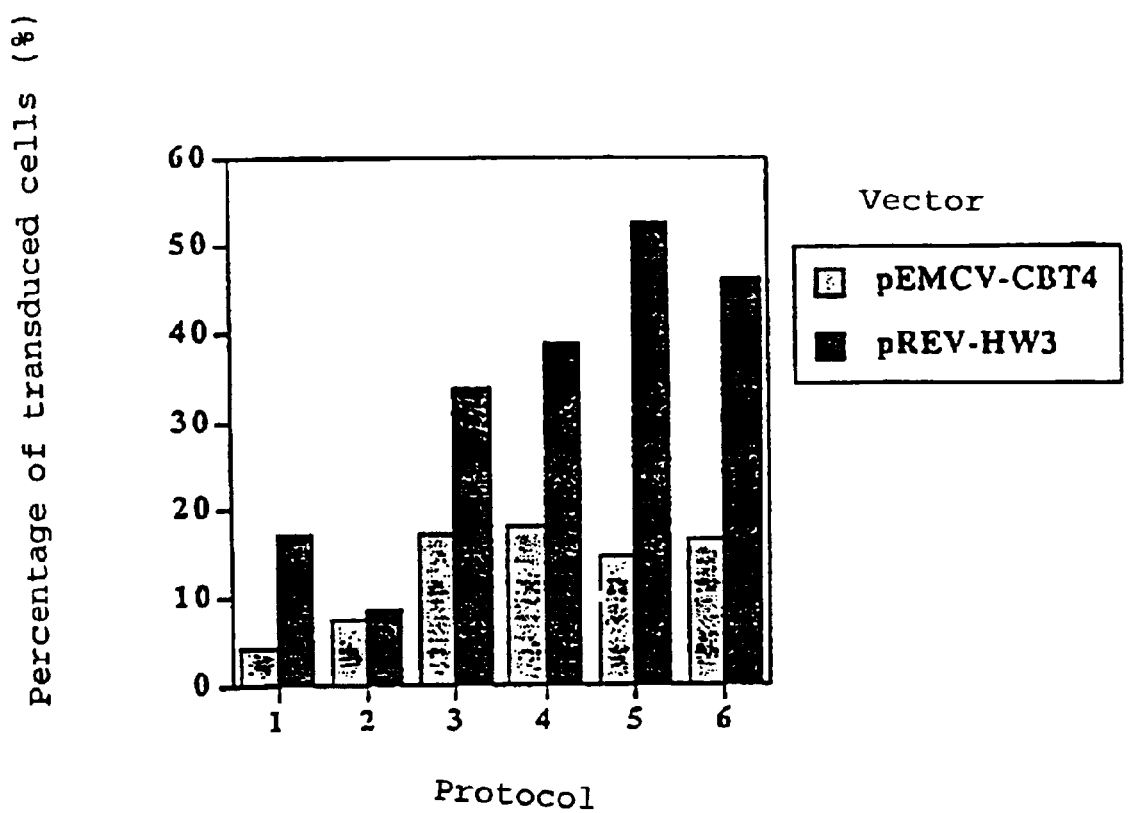
- Figure 5 -

SEQUENCE LISTING

<160> NUMBER OF SEQ ID NOS: 2

<210> SEQ ID NO 1
<211> LENGTH: 940
<212> TYPE: RNA
<213> ORGANISM: Reticuloendotheliosis virus

<400> SEQUENCE: 1

```
aaugugggag ggagcuccgg ggggaauagc gcuggcucgc uaacugccau auuagcuucu      60
guaaucaugc uugcuugccu uagccgccau uguacuugau auauuucgcu gauaucauuu     120
cucggaaucg gcaucauuuc ucggaaucgg caucaagagc aggcucauag accauaaaag    180
gaaauguucg uuggaggcga gcaucagacc acuugcgcca uccaaucacg agcaaacacg    240
agaucgaacu aucauacuga gccaaugguu guaaagggca gaugcuaucc uccaaugagg   300
gaaaauguca ugcaacaucc uguccuguaa gcggcuauau aagccaggug caucucuugc  360
ucggggucgc cguccuacac auuguuguga cgcgcggccc agauucgaau cuguaauaaa   420
aguuuuuuuc uucuauauuc ucagauuggc agugagagga gauuuuguuc gugguguagg   480
cuggccuacu ggguggggua gggguccgga cugaauccgu aguauuucga uacaacauuu   540
gggggcucgu ccgggauucc ucccaucgg cagaagugcc uacuguuucu ucgaacuccg   600
gcgccgguaa guaaguacuu gauuuuggua ccucgcgagg guuugggagg aucggagugg   660
cgggacgcug ccgggaagcu ccaccuccgc ucagcagggg acgcccugau cugagcucug   720
ugguaucuga uuguuguugg accgucucca agacggugau aauauaaguc gugguuugug   780
uguuuguuug uuaccuugug uuuguucguc acuugucgac agcgcccugc gaauuggugu   840
gcccacaccg cgcggcuugc gaauaauacu uuggagaguc uuuugccucc agugucuucc   900
guuuguacuc guccuccucu cccucuccgg ccgggaguggg                        940
```

<210> SEQ ID NO 2
<211> LENGTH: 578
<212> TYPE: RNA
<213> ORGANISM: Reticuloendotheliosis virus

<400> SEQUENCE: 2

```
gggggucgccg uccuacacau uguugugacg cgcggcccag auucgaaucu guaauaaaag     60
uuuuuuucuu cuauauccuc agauuggcag ugagaggaga uuuuguucgu gguguaggcu    120
ggccuacugg guggggguagg gguccggacu gaauccguag uauuucgaua caacauuugg   180
gggcucgucc gggauuccuc cccaucggca gaagugccua cuguuucuuc gaacuccggc   240
gccgguaagu aaguacuuga uuuugguacc ucgcgagggu uugggaggau cggaguggcg   300
```

-continued

| | | | | | |
|---|---|---|---|---|---|
| ggacgcugcc | gggaagcucc | accuccgcuc | agcaggggac | gcccugaucu | gagcucugug | 360 |
| guaucugauu | guuguuggac | cgucuccaag | acggugauaa | uauaagucgu | gguuugugug | 420 |
| uuuguuuguu | accuuguguu | uguucgucac | uugucgacag | cgcccugcga | auuggugugc | 480 |
| ccacaccgcg | cggcuugcga | auaauacuuu | ggagagucuu | uugccuccag | ugucuuccgu | 540 |
| uuguacucgu | ccuccucucc | cucuccggcc | gggauggg | | | 578 |

INTERNAL RIBOSOME ENTRY SITE AND VECTOR CONTAINING SAME

The present invention relates to the use of a nucleotide sequence derived from the 5' end of the genomic RNA or of the proviral DNA of a reticuloendotheliosis virus as internal ribosome entry site (IRES) and/or for improving retroviral encapsidation. More particularly, it relates to expression vectors comprising this sequence and in particular polycistronic vectors allowing the effective and stable expression of several genes of interest under the control of the same promoter. The present invention finds an advantageous application in the field of vectors for gene therapy.

BACKGROUND OF THE INVENTION

The feasibility of gene therapy applied to humans no longer needs to be demonstrated, and this relates to numerous therapeutic applications such as genetic diseases, infectious diseases and cancers. Numerous prior art documents describe the means using gene therapy, in particular by means of viral vectors. The vectors are generally obtained by deletion of at least part of the viral genes which are replaced by the therapeutic genes of interest. Such vectors can be propagated in a complementation line which provides in trans the viral functions deleted in order to generate a viral particle defective for replication but capable of infecting a host cell. To date, retroviral vectors are among the most widely used but there may also be mentioned vectors derived from adenoviruses, adeno-associated viruses, pox viruses and herpes viruses. This type of vectors, their organization and their mode of infection are widely described in the literature accessible to persons skilled in the art.

As a guide, the retroviral genome consists of a single-stranded linear RNA of positive polarity. In addition to the regulatory sequences R and U5 and U3 and R present at the 5' and 3' ends respectively, it carries three genes: gag encoding the capsid proteins, pol encoding reverse transcriptase and integrase and env encoding the envelope proteins. The encapsidation signals, situated upstream of the U5 sequences up to the beginning of the coding region of the gag gene, participate in the dimerization and the encapsidation of the viral RNA into the viral particles. The 5' end of the genome comprises a cap and the 3' end is polyadenylated. During the infectious cycle, the viral RNA is converted to a double-stranded linear proviral DNA provided at each end with inverted repeat sequences LTR (for Long Terminal Repeat) which are necessary for the initiation of transcription. The latter, which is carried out by the cellular machinery, allows the production of genomic and subgenomic RNAs from which the viral proteins are synthesized. Retroviruses may be classified into 4 subgroups A to D, on the basis of their morphology. Type C groups together the majority of retroviruses including the MLV (Murine Leukemia Virus) and MSV (Murine Sarcoma Virus) viruses used in most of the gene therapy vectors and the REV viruses (Reticuloendotheliosis Virus) from which the nucleotide sequence of the present invention is derived.

It may be advantageous to have gene therapy vectors which are more effective and capable in particular of efficiently producing several proteins of interest. However, the presence of several promoters within the same vector very often results in a reduction or even in a loss of expression over time. This is due to a well known phenomenon of interference between the promoter sequences. In this context, the publication of international application WO 93/03143 provides a solution to this problem which consists in using an internal ribosome entry site (IRES). It describes a dicistronic retroviral vector for the expression of two genes of interest placed under the control of the same promoter. The presence of a picornavirus IRES site between them allows the production of the product of expression derived from the second gene of interest by internal initiation of the translation of the dicistronic mRNA.

Normally, the entry of the ribosomes at the level of the messenger RNA (mRNA) occurs via the cap situated at the 5' end of all eukaryotic mRNAs. The 40S ribosomal subunits move along the RNA until an appropriate AUG codon is encountered in order to start the protein synthesis. Generally, the initiation takes place at the level of the first AUG codon. However, if the latter is in a context which is not very favorable, the 40S subunits continue up to a subsequent AUG codon situated in a better translational context (Kozak, 1984, Nucleic Acid Res. 12, 3873–3893; Kozak, 1991, J. Biol. Chem. 266, 19867–19870; Pain, 1996, Eur. J. Biochem. 236, 747–771).

However, there are exceptions to this universal rule. The absence of a cap in certain viral mRNAs suggests the existence of alternative structures allowing the entry of the ribosomes at an internal site of these RNAs. To date, a number of these structures, called IRESs because of their function, have been identified in the noncoding 5' region of noncapped viral mRNAs such as that in particular of the picornaviruses such as the poliomyelitis virus (Pelletier et al., 1988, Mol. Cell. Biol. 8, 1103–1112) and EMCV (Encephalomyocarditis virus (Jang et al., 1988, J. Virol. 62, 2636–2643). Cellular mRNAs possessing IRES elements have also been described. There may be mentioned those encoding the BIP protein (for Immunoglobulin heavy chain binding protein; Macejak and Sarnow, 1991, Nature 353, 90–94), certain growth factors (Teerink et al., 1995, Biochem. Biophy. Acts 1264, 403–408; Vagner et al., 1995, Mol. Cell. Biol. 15, 35–44), the translational initiation factor eIF4G (Gan and Rhoads, 1996, J. Biol. Chem. 271, 623–626) and two yeast transcriptional factors TFIID and HAP4 (Iizuka et al., 1994, Mol. Cell. Biol., 14, 7322–7330). IRES sites have also been demonstrated in the VL30-type murine retrotransposons (Berlioz et al., 1995, J. Virol. 69, 6400–6407) and, more recently in the mRNAs encoding the gag precursor of the Friend (FMLV) and Moloney (MoMLV) murine leukemia viruses (Berlioz and Darlix, 1995, J. Virol. 69, 2214–2222; Vagner et al., 1995, J. Biol. Chem. 270, 20376–20383).

DETAILED DESCRIPTION OF THE INVENTION

A new internal ribosome entry site has now been found in the noncoding 5' region of the RNA of the avian reticuloendotheliosis virus (REV) type A (REV-A) and its efficiency for initiating the translation of coding sequences placed after it in a monocistronic or dicistronic manner has been shown.

The IRES site of the present invention is particularly advantageous compared with those already described in the literature. In the first place, it allows a high level of expression of the cistron which it controls. In addition and, unexpectedly, it can also, within the framework of a retroviral vector, contribute or improve, in association with an appropriate encapsidation region, the dimerization or encapsidation functions, allowing an increase in the viral titer. And finally, because of its weak homology with the murine retrovirus sequences used in most of the gene therapy vectors intended for human use, its use considerably reduces the risk of production of replication-competent viruses.

Most of the gene therapy protocols approved by the RAC (Recombinant DNA Advisory Committee) in the United States use vectors derived from the MoMLV virus. Currently, the choice of a specific retroviral vector for a given therapeutic application remains empirical and the factors influencing the viral titer and the expression of the genes have not yet been clearly elucidated. The study of the cis-acting sequences which control the encapsidation and the establishment of the relative strengths of the various IRES elements can make it possible to optimize the gene therapy vectors in terms of titer and gene expression. One of the aims of the present invention is to provide new retroviral vectors capable of being propagated at a high titer and of allowing optimal expression of one or more genes of interest.

Accordingly, the subject of the present invention is the use of a nucleotide sequence derived from all or part of the 5' end of the genomic RNA of a type C retrovirus with the exception of the Friend (FMLV) and Moloney (MoMLV) murine leukemia viruses, as internal ribosome entry site (IRES) in a vector and/or for allowing or improving the encapsidation of a retroviral vector.

Nucleotide sequence is understood to mean a sequence composed of ribo-(RNA) or deoxyribonucleotides (DNA). Within the framework of the present invention, the 5' end of the genomic RNA of a retrovirus corresponds to the 5' quarter of said RNA which extends from the site of initiation of transcription (nucleotide +1) to about 2 kb in the 3' direction. The term retrovirus is widely defined in basic virology manuals accessible to persons skilled in the art and the essential characteristics have been summarized as a guide above. The term "derived" refers to a sequence having a type C retroviral origin, but which may have undergone at least one modification in relation to the native sequence. The modification(s) which may be envisaged include the deletion, addition, substitution and/or mutation of one or more nucleotides (nt). Such modifications may be designed, for example, to increase the IRES function, the encapsidation function or the function of introducing suitable restriction sites in order to facilitate subsequent cloning steps. The term "derivative" also comprises the DNA equivalent of the genomic RNA in a modified or unmodified form.

IRES denotes a site capable of promoting the entry of the ribosomes into an RNA molecule in a manner independent of the cap. In accordance with the aims pursued by the present invention, the IRES function can be exerted in any expression cassette or vector. A sequence in use within the framework of the present invention may also act as element activating the encapsidation of retroviruses or retroviral vectors by promoting the dimerization of two copies of the retroviral genome and/or the encapsidation of the dimer into the viral particles. According to a preferred embodiment, said sequence is capable of exerting an IRES function and of improving the encapsidation function when it is introduced into an appropriate retroviral vector.

A nucleotide sequence as used within the framework of the present invention may be isolated from the 5' end of the genomic RNA or of the proviral DNA of a type C retrovirus or of any state of the art plasmid carrying the retroviral fragment of interest. It goes without saying that it can be generated by any technique used in the art, for example by cloning with the aid of appropriate probes, by PCR (Polymerase Chain Reaction) or alternatively by chemical synthesis. Advantageously, said sequence comprises all or part of the region which follows the U3 domain of the 5' LTR, up to the initiator AUG codon of the gag gene. For the purposes of the present invention, it comprises at least 50 nucleotides, advantageously at least 100 nucleotides, preferably at least 200 nucleotides and preferably at least 300 nucleotides included in said 5' end. However, it can of course extend beyond in the 5' or 3' direction or comprise additional sequences. Advantageously, said sequence comprises from 100 to 1500 nucleotides and, in particular, from 300 to 800 nucleotides.

It is preferable to use within the framework of the present invention a type C retrovirus with the exception of the FMLV and MoMLV viruses. A type C retrovirus which is more particularly suitable is selected from the REV (reticuloendotheliosis virus) and MSV (murine sarcoma virus) viruses and in particular the Moloney (MMSV), MHV (*Mus hortulanus* virus), MEV (mouse endogenous retrovirus), FMOV (FBR murine osteosarcoma virus), AMLV (AKV murine leukemia virus), MEELV (mouse endogenous ecotropic murine leukemia virus), SFFV (Friend spleen focus-forming virus), RASV (rat sarcoma virus), FLV (Feline leukemia virus), FSV (feline sarcoma virus), EFLV (cat endogenous proviral feline leukemia virus), SSV (Simian sarcoma virus), GALV (gibbon ape leukemia virus) and BAEV (baboon endogenous virus) viruses.

According to a most preferred embodiment, a nucleotide sequence used in the present invention is derived from all or part of the 5' end of the genomic RNA of a reticuloendotheliosis virus (REV). The REV viruses comprise in particular various A, B and T sub-types as well as the DIAV (duck infectious anemia virus), SNV (spleen necrosis virus) and CSV (chick syncytial virus) viruses (see for example Encyclopedia of Virology, 1994, Enrietto, Reticuloendotheliosis viruses, p. 1227–1232 Ed. R. Webster and A. Granoff, Academic Press, Hartourt Brace § Company Publishers). An REV virus which is most particularly suitable is the avian reticuloendotheliosis virus, in particular the type A virus (REV-A).

According to the latter variant, a nucleotide sequence comprising at least 100 nucleotides and at most 800 nucleotides (nt) of the noncoding SI end of the REV-A virus and more particularly a nucleotide sequence which is substantially homologous or identical to all or part of the sequence presented in the sequence identifier SEQ ID NO: 1 will be preferably used. As preferred examples, there may be mentioned a nucleotide sequence which is substantially homologous or identical to the sequence presented in the sequence identifier SEQ ID NO: 2:

(i) starting at nucleotide 1 and ending at nucleotide 578,
(ii) starting at nucleotide 265 and ending at nucleotide 578, or
(iii) starting at nucleotide 452 and ending at nucleotide 578.

The term substantially homologous refers to a degree of homology greater than 70%, advantageously greater than 80%, preferably greater than 90% and, most preferably, greater than 95%. As already indicated, said nucleotide sequence may have a sequence which is slightly different from that described in SEQ ID NO: 1 or 2, provided, however, that the modification(s) does (do) not affect its IRES and/or encapsidation functions.

According to an advantageous mode, the nucleotide sequence used within the framework of the present invention is identical to the sequence presented in the sequence identifier SEQ ID NO: 2:

(i) starting at nucleotide 1 and ending at nucleotide 578,
(ii) starting at nucleotide 265 and ending at nucleotide 578, or
(iii) starting at nucleotide 452 and ending at nucleotide 578.

The IRES function of said nucleotide sequence is particularly advantageous in a context low in magnesium ion, for example in a cellular context. A high concentration of $Mg^{2+}$ ions may reduce the efficiency of the initiation of translation mediated by the sequence.

A nucleotide sequence used in the present invention is more particularly intended to be integrated into a vector for the transfer and expression of one or more genes of interest. The choice of such a vector is wide and the techniques for cloning into the vector chosen are within the capability of persons skilled in the art. In accordance with the aims pursued by the present invention, it is possible to envisage a plasmid vector or a vector derived from an animal virus and, in particular, from a poxvirus (canarypox or vaccinia virus, in particular Copenhage or MVA), adenovirus, baculovirus, herpesvirus, adeno-associated virus or retrovirus. Such vectors are widely described in the literature. In particular, when an adenoviral vector is used, it may be derived from a human adenovirus (preferably type 2 or 5), an animal adenovirus (preferably canine or bovine) or alternatively from a hybrid between a variety of species. The general technology relating to adenoviruses is disclosed in Graham and Prevec (1991, Methods in Molecular Biology, Vol. 7, Gene Transfer and Expression Protocols; Ed. E. J. Murray, the Human Press Inc., p. 109–118).

In accordance with the aims pursued within the framework of the present invention, said nucleotide sequence is preferably positioned upstream of a gene of interest in order to enhance the translation of the product of expression for which it codes. It may be used in an expression cassette of the monocistronic type (for the expression of a gene of interest placed under the control of a promoter) or polycistronic type (for the expression of at least two genes of interest placed under the control of the same promoter). The latter may contain several elements in tandem "IRES site-gene of interest" in which at least one of the IRES sites consists of a nucleotide sequence as defined above. The use in a dicistronic cassette, either upstream of the first gene of interest or upstream of the second, is most particularly preferred, the latter variant being preferred.

When a vector according to the invention comprises several expression cassettes, they may be inserted in any orientation relative to each other, either in the same orientation (promoter acting in the same direction) or in reverse orientation (promoter acting in an opposite orientation). Moreover, a vector according to the invention may comprise several nucleotide sequences used according to the invention. In this case, it is preferable that they are derived from different type C retroviruses.

According to a most preferred embodiment, a vector according to the invention is derived from a retrovirus. There may be mentioned, by way of examples, the avian retroviruses such as the avian erythroblastosis virus (AEV), the avian leukemia virus (AVL), the avian sarcoma virus (ASV), the spleen necrosis virus (SNV) and the Rous sarcoma virus (RSV), the bovine retroviruses, the feline retroviruses (FLV, FSV and the like), the murine retroviruses such as the murine leukemia virus (MuLV), the Friend virus (FMLV) and the murine sarcoma virus (MSV) and the primate retroviruses (GALV, FSV, BAEV and the like). Of course, other retroviruses may be used. However, the use of the MoMLV virus is most particularly preferred. The numerous retrovirus vectors described in the literature can be used within the framework of the present invention.

The retroviral vectors which may be envisaged for the purposes of the present invention comprise at least the following elements associated in a functional manner: a retroviral 5' LTR and a retroviral 3' LTR, one or more genes of interest, and the nucleotide sequence used within the framework of the present invention to allow or improve the encapsidation of said vector into a viral particle and/or as an IRES site to allow or promote the expression of a gene of interest positioned downstream of said nucleotide sequence. It goes without saying that the retroviral 5' LTR may be used as a promoter, but it is also possible to use an internal promoter. Moreover, the 5' and possibly 3' LTR may have the same retroviral origin (for example REV) as the nucleotide sequence, or a different origin. For example, a monocistronic vector will comprise, from 5' to 3', a 5' LTR, the nucleotide sequence, a gene of interest and a 3' LTR.

Of course, a retroviral vector according to the invention may also comprise a conventional encapsidation region (E+). However, the presence of the latter is not required when the nucleotide sequence used in the present invention can itself exert the encapsidation function. Such an embodiment may be more particularly envisaged when the retroviral 5' LTR is derived from an REV virus and, preferably from SNV, and the nucleotide sequence is substantially homologous or identical to the sequence presented in SEQ ID NO: 2, starting at nt 1 and ending at nt 578 or starting at nt 265 and ending at nt 578.

According to an advantageous embodiment, a retroviral vector according to the invention comprises at least:

(a) a retroviral 5' LTR,
(b) an encapsidation region,
(c) optionally, a first gene of interest followed by an internal promoter region of different origin from that of said retroviral 5' LTR,
(d) a second gene of interest,
(e) an IRES site,
(f) a third gene of interest, and
(g) a retroviral 3' LTR,
at least one of the encapsidation region and the IRES site consisting of said nucleotide sequence used according to the invention.

In the case where the retroviral vector according to the invention comprises an expression cassette directed by an internal promoter region, it is preferable, in order to promote gene expression, that the latter is in an opposite orientation relative to the retroviral 5' and 3' LTRs. It is also possible to include other elements, for example another IRES site and another gene of interest or another expression cassette.

A preferred retroviral vector according to the invention comprises an encapsidation region which is derived from a murine retrovirus, especially from an MoMLV, or from a VL30-type retrotransposon and an IRES site comprising a nucleotide sequence which is substantially homologous or identical to the sequence presented in the sequence identifier SEQ ID NO: 2:

(i) starting at nucleotide 1 and ending at nucleotide 578,
(ii) starting at nucleotide 265 and ending at nucleotide 578, or
(iii) starting at nucleotide 452 and ending at nucleotide 578.

There may be mentioned in particular the pREV HW-3 and HW-6 type dicistronic retroviral vectors in which the encapsidation region is derived from an MoMLV and the IRES site consists of a nucleotide sequence identical to the sequence presented in SEQ ID NO: 2 starting at nucleotide 265 and ending at nucleotide 578 or starting at nucleotide 452 and ending at nucleotide 578. Of course, persons skilled in the art can vary the genes of interest according to the desired therapeutic effect.

For the purposes of the present invention, a gene of interest used in the invention may be obtained from a eukaryotic organism, prokaryotic organism or a virus by any conventional molecular biological technique. It can encode a polypeptide corresponding to a native protein as found in nature, homologous to the host cell or otherwise, a protein fragment, a chimeric protein obtained from the fusion of polypeptides of various origins or a mutant having improved and/or modified biological properties. Such a mutant may be generated by substitution, deletion and/or addition of one or more amino acid residues. In addition, the polypeptide may be (i) intracellular (ii) membranous, present at the surface of the host cell or alternatively (iii) secreted outside the host cell and may therefore comprise appropriate additional elements, such as a sequence encoding a secretory signal or a region for transmembrane anchorage.

The use of a therapeutic gene of interest encoding a product of expression capable of inhibiting or retarding the establishment and/or the development of a genetic or acquired disease is most particularly preferred. A vector according to the invention is particularly intended for the prevention or treatment of cystic fibrosis, hemophilia A or B, Duchenne's or Becker's myopathy, cancer, AIDS, cardiovascular diseases (restenosis, arteriosclerosis, ischemia and the like) and other infectious diseases due to a pathogenic organism: virus, bacterium, parasite or prion. The genes of interest which can be used in the present invention are those which encode the following proteins:

- a cytokine and especially an interleukin (IL-2, IL-7, IL-10, IL-12 and the like), an interferon, a tissue necrosis factor and a growth, and especially hematopoietic, factor (G-CSF, GM-CSF),
- a factor or cofactor involved in coagulation and especially factor VIII, factor IX, von Willebrand's factor, antithrombin III, protein C, thrombin and hirudin,
- an enzyme and especially trypsin, a ribonuclease, alkaline phosphatase (plap) and β-galactosidase,
- an enzyme inhibitor such as α1-antitrypsin and viral protease inhibitors
- a product of expression of a suicide gene such as thymidine kinase of the HSV virus (herpesvirus) type I, that of the fur1 and/or fcy1 gene of *Saccharomyces cerevisiae*, ricin,
- an activator or an inhibitor of ion channels,
- a protein whose absence, modification or the deregulation of whose expression is responsible for a genetic disease, such as the CFTR protein, dystrophin or minidystrophin, insulin, ADA (adenosine diaminose), gluco-cerebrosidase and phenylhydroxylase,
- a protein capable of inhibiting the initiation or the progression of cancer, such as the products of expression of the tumor suppressor genes, for example the p53, p73 and Rb genes,
- a protein capable of stimulating an immune response, an antibody, the antigens of the major histocompatibility complex or an immunotoxin,
- a protein capable of inhibiting a viral infection or its development, for example the antigenic epitopes of the virus in question or altered variants of viral proteins capable of entering into competition with the native viral proteins,
- a cellular or nuclear receptor or one of their ligand,
- a growth factor (FGF for Fibroblast Growth Factor, VEGF for Vascular Endothelial cell Growth Factor and the like), and
- an inducer of apoptosis (Bax and the like), an inhibitor of apoptosis (Bcl2, BclX and the like), a cytostatic agent (p21, p16, Rb and the like), a nitric oxide synthase (NOS), an apolipoprotein (apoAI, apoE and the like), a catalase, an SOD, a factor acting on angiogenesis (PAI for Plasminogen Activator Inhibitor and the like).

Moreover, a gene of interest used in the present invention may also encode a selectable marker which makes it possible to select or identify the host cells transfected with a vector according to the invention. There may be mentioned the neo (neomycin) gene which confers resistance to the antibiotic G418, the dhfr (dihydrofolate reductase) gene, the CAT (Chloramphenicol Acetyl Transferase) gene or alternatively the gpt (xanthine phosphoribosyl) gene.

In general, a promoter which is functional in the host cell considered and, preferably, a human cell will be used for the expression of one or more genes of interest. The choice of the promoter is very broad and within the capability of persons skilled in the art. It may be a promoter which naturally controls the expression of a gene of interest used in the present invention or any other promoter of any origin. Moreover, it may be of a constitutive nature or of a regulatable nature, especially in response to certain tissue-specific or events-specific cellular signals. For example, it may be advantageous to target the expression of the gene of interest at the level of the lymphocytic cells in the case of AIDS, of pulmonary cells in the case of cystic fibrosis or of muscle cells in the case of myopathies.

By way of examples, the promoters which are suitable within the framework of the present invention may be chosen from the SV40 (Simian Virus 40), CMV (Cytomegalovirus), HMG (Hydroxymethyl-Glutaryl Coenzyme A) and TK (Thymidine kinase) promoters, the retroviral LTRs such as that of the MoMLV, RSV or MSV when a retroviral vector is used, the adenoviral promoters E1A and late MLP (Major Late Promoter) especially in the context of an adenoviral vector, the 7.5K, H5R, pK1L, p28 and p11 promoters intended for poxvirus vectors such as the vaccinia virus, the PGK promoter (Phosphoglycerokinase), the liver-specific promoters of the genes encoding α1-antitrypsin, factor IX, albumin and transferrin, the promoters of the immunoglobulin genes which allow expression in the lymphocytes, and finally the promoters of the genes encoding the surfactant or the CFTR protein which exhibit a degree of specificity for the pulmonary tissues. They may also be a promoter which stimulates expression in a tumor or cancer cell. There may be mentioned in particular the promoters of the MUC-1 gene which is overexpressed in breast and prostate cancers (Chen et al., 1995, J. Clin. Invest. 96, 2775–2782), CEA (for carcinoma embryonic antigen) gene which is overexpressed in colon cancers (Schrewe et al., 1990, Mol. Cell. Biol. 10, 2738–2748), tyrosinase gene which is overexpressed in melanomas (Vile et al., 1993, Cancer Res. 53, 3860–3864), ERB-2 gene which is overexpressed in cancers of the breast and the pancreas (Harris et al., 1994, Gene Therapy 1, 170–175), α-fetoprotein which is overexpressed in liver cancers (Kanai et al., 1997, Cancer Res. 57, 461–465), APC which is overexpressed in colorectal cancers, BRCA-1 and 2 (Wooster et al., 1995, Nature 378, 789–792) which are overexpressed in ovarian cancers and PSA (for prostate specific antigen) which is overexpressed in prostate cancers.

Moreover, the gene of interest used in the present invention may comprise other sequences which improve its expression, both at the level of transcription and of translation; for example, an enhancer-type transcriptional activator sequence, an intron sequence, a transcriptional termination signal (polyA) and, as indicated above, a secretory signal or a transmembrane region.

The invention also covers the viral particles generated from a viral vector according to the invention. The procedure is generally carried out by transfecting the latter into an appropriate cell line. If the viral vector used is replication-defective, a complementation line will be used. In general, persons skilled in the art know the lines which can be used to generate infectious viral particles as well as the method to be used depending on the vector used.

For example, in the case of an adenoviral vector, the 293 line may be used (Graham et al., 1977, J. Gen. Virol., 36, 59–72). As regards a retroviral vector, the use of ecotropic cell lines, such as the CRE line (Danos and Mulligan, 1988, Proc. Natl. Acad. Sci. USA, 85, 6460–6464) or GP+E-86 line (Markowitz et al., 1988, J. Virol., 62, 1120–1124) may be envisaged. However, the use of an amphotropic complementation line such as the PG13 line (Miller et al., 1991, J. Virol., 65, 2220–2224) or Psi Env-am line (Markowitz et al., 1988, T.A.A.P. Vol. CI, 212–218) is most particularly preferred. Generally, the infectious viral particles are recovered in the culture supernatant for the transfected complementation cells.

The invention also extends to the cells comprising a vector according to the invention or infected with infectious viral particles according to the invention. The methods of transfection are well known to persons skilled in the art. There may be mentioned the technique of precipitation with calcium phosphate, that with DEAE-dextran, microinjection or encapsulation into lipid vehicles. Moreover, the vectors according to the invention may be present in the host cell in a form integrated into the cellular genome or in the form of episomes both in the nucleus and in the cytoplasm. The cell according to the invention is advantageously a eukaryotic cell, especially a mammalian cell and, preferably, a human cell. It may be a primary or tumor cell of hematopoietic origin (totipotent stem cell, leucocyte, lymphocyte, monocyte, macrophage and the like), hepatic origin, epithelial origin, fibroblast, from the central nervous system and, most particularly, a muscle cell (myoblast, myocyte, satellite cell, smooth muscle cell and the like), cardiac cell, vascular cell, trachea cell, pulmonary cell or cell from the central nervous system.

The present invention also relates to the therapeutic use of a vector, of a viral particle or of a cell according to the invention, for the preparation of a pharmaceutical composition intended for the treatment and/or for the prevention of a disease which is treatable by gene therapy, especially of a genetic disease, of an acquired disease such as cancer or of an infectious disease.

However, such a use is not limited to an application of the somatic gene therapy type. In particular, a vector according to the invention may be used for other purposes such as the production, by the recombinant route in prokaryotic or eukaryotic cells, of product(s) of expression encoded by at least one of the genes of interest. For example, it is possible to envisage the coexpression of two genes of interest in a dicistronic expression vector using a nucleotide sequence according to the invention. The coexpression of a gene for resistance to an antibiotic as a second cistron may make it possible to increase the expression of a first cistron. It is possible to obtain a mature product by coexpression of two genes for which the product of expression of one allows the maturation of the polypeptide encoded by the other (for example polypeptide precursor and a protease cleaving the precursor into a mature polypeptide). In this case, it is possible to use prokaryotic cells (*E. coli* and the like), lower eukaryotic cells (yeast, fungus, insect and the like) or animal cells. Said product of expression of interest will then have to be harvested and optionally purified from the supernatant or from the cell culture by conventional techniques. Another possible use consists in the production of transgenic animals which have integrated into their genome a cassette for the expression of one or more genes of interest and comprising a nucleotide sequence according to the invention. These may be mice, rats, rabbits, fish, primates or farm animals (bovines, ovines, porcines and the like). The techniques for generating these transgenic animals are known. The polypeptide of interest may be recovered in a conventional manner, for example, from the biological fluids (blood, milk and the like) of the animal.

The invention also relates to a pharmaceutical composition comprising, as therapeutic or prophylactic agent, a vector, a viral particle or a cell according to the invention or a polypeptide of interest obtained in accordance with the use according to the invention, in combination with a pharmaceutically acceptable vehicle.

A pharmaceutical composition according to the invention may be manufactured in a conventional manner. In particular, a therapeutically effective quantity of such an agent is combined with a carrier, a diluent or an adjuvant which is acceptable. It may be administered by any route of administration, in a single dose or in a dose repeated after a certain time interval. The intravenous, intramuscular, intrapulmonary (optionally by aerosolization) or intratumor administration will be preferred. The quantity to be administered will be chosen according to various criteria, in particular the use as a treatment or as a vaccine, the route of administration, the patient, the type of disease to be treated and its state of progression, the duration of the treatment, the vector selected and the like. As a guide, a pharmaceutical composition according to the invention comprises between $10^4$ and $10^{14}$ pfu (plaque forming unit), advantageously between $10^5$ and $10^{13}$ pfu and, preferably, between $10^6$ and $10^{11}$ pfu of viral particles. A vector-based composition may be formulated in the form of doses comprising from 0.01 to 100 mg of DNA, preferably from 0.05 to 10 mg and most preferably from 0.1 to 5 mg.

The formulation may also include, alone or in combination, a diluent, an adjuvant or an excipient which is pharmaceutically acceptable, as well as a solubilizing, stabilizing or preserving agent. The composition may be presented in a single dose or in multidoses in liquid form or in dry form (freeze-dried product and the like) which can be reconstituted immediately before use with an appropriate diluent.

Moreover, the invention relates to a method of treating genetic diseases, cancers and infectious diseases according to which a therapeutically effective quantity of a vector, of a viral particle or of a cell according to the invention is administered to a patient requiring such a treatment. According to a first therapeutic protocol, they can be administered directly in vivo, for example by intravenous injection, intramuscular injection, intratumor injection or by aerosolization into the lungs. Alternatively, it is possible to adopt an ex vivo gene therapy protocol which consists in collecting the cells from a patient (bone marrow stem cells, peripheral blood lymphocytes and the like), in transfecting them with a vector according to the invention and in culturing them in vitro before reimplanting them into the patient.

Finally, the invention relates to the use of a vector, of a viral particle or of a pharmaceutical composition according to the invention for the transfection or infection of pluripotent cells, especially pluripotent cells of the central nervous system.

BRIEF DESCRIPTION OF THE DRAWINGS

The invention is illustrated below with reference to the following figures.

FIG. 1 is a schematic representation of the monocistronic plasmids used as template for the in vitro synthesis of capped and noncapped RNAs. They contain the cytomegalovirus early promoter (Po CMV) which can be used for the in vivo expression, the promoter of the gene encoding the T7 phage RNA polymerase (Po T7) which can be used for the in vitro experiments, various portions of the untranslated 5' end (leader) of the REV-A virus (1 to 578 for pREV CB-95, 578 to 1 for pREV CG-53, 1 to 578 deleted for nt 268 to 452 for pREV CG-54, 265 to 578 for pREV CG-55 and 452 to 578 for pREV CG-56) and the LacZ gene (ΔLacZ) encoding a β-galactosidase truncated at the C-terminal end with a molecular mass of about 46 kDa.

FIG. 2 is a schematic representation of the dicistronic plasmids used as template for the in vitro synthesis of capped and noncapped RNAs. They contain the cytomegalovirus early promoter (Po CMV) which can be used for the in vivo expression, the promoter of the gene encoding the T7 phage RNA polymerase (Po T7) which can be used for the in vitro experiments, the neo gene, various portions of the untranslated 5' end (leader) of the REV-A virus (1 to 578 for pREV CB-54, 578 to 1 for pREV CG-50, 1 to 578 deleted for nt 268 to 452 for pREV CG-52, 265 to 578 for pREV CG-55 and 452 to 578 for pREV CG-58) and the LacZ gene (ΔLacZ) encoding a β-galactosidase truncated at the C-terminal end with a molecular mass of about 46 kDa.

FIG. 3A is a schematic representation of the dicistronic retroviral vectors possessing two elements of different retroviral origin, as IRES and as encapsidation region (E) and two genes of interest as reporter genes plap encoding placental alkaline phosphatase and neo encoding neomycin phosphotransferase. B) Retroviral vectors of the pREV HW series possessing LTRs derived from MLV and placed in a pBR322 plasmid context. VL30E+ corresponds to the untranslated 5' region of HaMSV and MoMLV E+ corresponds to the encapsidation region of MoMLV. C) Reference vector pEMCV-CBTV having LTRs and the encapsidation region of MoMLV and the IRES of EMCV. In all cases, the sequences are numbered relative to the cap site (position +1) of the genomic RNA.

FIG. 4 illustrates the effect of rapamycin on the activities A) alkaline phosphatase and B) neomycin phosphotransferase which are produced in the GP+E-86 cells which are not transfected or which are stably transfected with the various vectors pREV HW or pEMCV-CBTV (pCB100) and treated with rapamycin (filled boxes) or not treated (control, dotted boxes).

FIG. 5 illustrates the optimization of the transduction protocol applied to the neuroectodermal cells Dev. The percentage of Dev cells transduced with the pEMCV-CBTV virus (IRES EMCV) and pREV HW-3 virus (IRES REV-A) is determined by flow cytometry.

EXAMPLES

The constructions described below are carried out according to the general genetic engineering and molecular cloning techniques detailed in Sambrook et al. (1989, Molecular cloning: A Laboratory Manual, 2nd ed, Cold Spring Harbor Laboratory Press, Cold Spring Harbor, N.Y.) or according to the manufacturer's recommendations when a commercial kit is used. The PCR techniques are known to persons skilled in the art and are widely described in PCR protocols, a guide to methods and applications (Ed: Innis, Gelfand, Sninsky and White, Academic Press, Inc.). The amplifications of plasmid DNA are carried out in *Escherichia coli* HB101 strain 1035 (recA$^-$). Moreover, the position of the REV-A sequences used in the constructions is indicated with reference to the RNA molecule, position +1 corresponding to the first nucleotide of the RNA molecule, that is to say to the site of initiation of transcription (Darlix et al., 1992, J. Virol. 66: 7245–7252).

Example 1

Identification of an IRES Site at the Level of the Leader 5' End of the REV-A RNA Studies of protein synthesis in vitro were initiated with the aid of a series of mono- and dicistronic plasmids containing fragments of the 5' leader of the REV-A genomic RNA in order to determine if they allow the translation of cistrons by internal binding of ribosomes.

1. Construction of the Mono- and Dicistronic Plasmids

The DNA fragments corresponding to sequences 1 to 578, 265 to 578 and 452 to 578 of the REV-A RNA are isolated by PCR from the pREVSC-1 template (Darlix et al., 1992, J. Virol. 66, 7245–7252). Appropriate primers which persons skilled in the art can design, provided at their ends with an NheI site, are used. After digestion with this enzyme, the PCR fragments are inserted upstream of the LacZ gene into the vector pEMCV-M260-837 (Berlioz et al., 1995, J. Virol. 69, 6400–6407) previously cleaved with NheI. The LacZ gene used encodes a β-galactosidase product truncated at the C-terminal end. The monocistronic plasmids pREV CB-95 (1–578), pREV CG-55 (265–578) and pREV CG-56 (452–578) illustrated in FIG. 1 are obtained. The discistronic plasmids pREV CB-54 (1–578), pREV CB-55 (265–578) and pREV CG-58 (452–578) are represented in FIG. 2 and result from the insertion of the preceding PCR fragments between the neo and LacZ genes of pEMCV-D260-837 (pCB101) (Berlioz et al., 1995, J. Virol. 69, 6400–6407) also digested with NheI. The amplification of nt 1 to 578 deleted for sequences 268 to 452 is carried out using the vector pREVSC-1 previously digested with KpnI and SacI, treated with the Klenow fragment of DNA polymerase of *E. coli* and re-ligated. The amplified fragment digested with NheI is cloned into pEMCV-M260-837 upstream of the LacZ gene or between the neo and LacZ genes of pEMCV-D260-837, both vectors having been digested with NheI, to give pREV CG-54 (FIG. 1) and pREV CG-52 (FIG. 2), respectively. Finally, the monocistronic control plasmids pREV CG-53 (FIG. 1) and dicistronic plasmids pREV CG-50 (FIG. 2) were constructed by introducing the PCR fragment carrying the REV-A sequences 1 to 578 into the preceding vectors in the opposite orientation (578-1). In all the constructs containing the REV-A sequences in the sense orientation, the initiation of translation of β-galactosidase is under the control of the AUG codon of the REV-A gag gene situated at position 574–576, whereas in the control plasmids, the synthesis of β-galactosidase depends on an AUG placed in a favorable Kozak context introduced by PCR.

2. Synthesis of RNA and Translation in vitro

The capped and noncapped RNAs are synthesized from 1 µg of plasmid DNA linearized with SspI (position 1240 in the LacZ gene) with the aid of the T7 RNA polymerase (mMessage mMachine™ or MAXIscript™, Ambion) in a reaction volume of 20 µl according to the protocol recommended by the supplier. The transcription is stopped by treating the DNA template with the DNaseI enzyme followed by precipitation of the RNAs in the presence of lithium chloride. The RNAs are taken up in 50 μl of TE buffer (10 mM Tris-HCl, pH 7.5, 1 mM EDTA) before being purified and desalted by passing over an S-300 MicroSpin™ column (Pharmacia BioTech) according to the supplier's recommendations. The integrity of the transcribed RNAs is checked by electrophoresis on a 0.7% agarose gel containing ethidium bromide (0.5 μg/ml). The final concentration of RNA is determined spectrophotometrically.

The capped and noncapped RNAs (10 μg/ml) are translated in the RRL cellular system (Promega) used at 50% of its initial concentration in the presence of 1 mCi of [$^{35}$S] methionine per ml (Amersham) at 31° C. for 1 h. The reaction medium is supplemented with potassium acetate at a final concentration of 120 mM. Moreover, the luciferase RNA is tested under the same reaction conditions (positive control). A test carried out in the absence of RNA constitutes the negative control. In parallel, the effect of the FMDV virus (Foot and Mouth disease virus) L protease on the translation of the dicistronic RNAs is tested. This protease cleaves the translation initiation factor eIF4G between glycine at position 479 and arginine at position 480 to generate two peptide fragments lacking initiator activity (Kirchweger et al., 1995, J. Virol. 68, 5677–5684). In addition, Ohlmann et al. (1995, Nucleic Acid Res. 23, 334–340; 1996, EMBO J. 15, 1371–1382) has shown that the treatment of reticulocyte lysates with L protease inhibits the in vitro translation of the capped cellular RNAs whereas the internal initiation directed by the IRES of the cardiovirus is not affected. Thus, if an IRES element exists in the REV-A 5' leader, the presence of L protease should not affect the expression of the cistron whose translation is under its control. In this case, the tests use the RRL Flexi system (Promega) at 50% of its initial concentration, 8 μg/ml of RNA, 1 mCi of [$^{35}$S] methionine per ml (Amersham) and 30 ng of recombinant L protease and purified by conventional methods. The reaction mixture is supplemented with potassium chloride at a final concentration of 80 mM. The reaction is continued at 31° C. for 1 h.

The samples are heat-denatured in 62.5 mM Tris-HCl pH 6.8, 2% sodium dodecyl sulfate (SDS), 10% glycerol, 5% β-mercaptoethanol and 0.02% bromophenol blue and the labeled proteins analyzed by electrophoresis on a 12% (weight/vol), 0.2% SDS, polyacrylamide gel. The product of the neo gene and β-galactosidase migrate to a molecular mass of about 28 and 46 kDa respectively. The capdependent and independent translation efficiency is quantified by scanography (Phospho-Imageur Storm 840, version 4.00, Molecular Dynamics; Image Quant™ version 1.1, Molecular Dynamics). In the case of the dicistronic vectors, the labeling intensity for the expression product of the second cistron (β-galactosidase) whose translation is mediated by the IRES is evaluated after standardization at the level of expression of the neo product.

It is observed that the translation of the noncapped RNAs obtained from the monocistronic plasmids pREV CB-95, pREV CG-53, pREV CG-54, pREV CG-55 and pREV CG-56 is as efficient as that of the capped RNAs. However, as expected, the quantity of β-galactosidase generated from the plasmid pREV CG-53 in which the REV-A sequences (1 to 578) are in the antisense orientation is much lower than that obtained with the constructs using an REV-A sequence in the sense orientation. When the REV-A fragments are used in a dicistronic manner between the neo and LacZ genes, the expression of β-galactosidase appears only in the presence of a functional IRES (pREV CB-54, pREV CB-55 and pREV CG-52) whereas that of the first cistron (neo) is efficient in all cases (including pREV CG-50). Comparative tests of in vitro translation carried out with the preceding vectors and the plasmid pEMCV-D260-837 comprising the reference EMCV IRES show that the REV-A 1–578, 265–578 and 452–578 fragments are capable of initiating the translation of the second cistron more efficiently than that directed by the EMCV IRES. Moreover, the treatment of the reticulocyte lysates with the L protease is accompanied by inhibition of the cap-dependent expression of the neo gene whereas the expression of β-galactosidase dependent on IRES is substantially increased. For the pREV CG-50 control, the inhibition of the neo expression is also observed whereas the expression of β-galactosidase is barely detectable whether the treatment with L protease takes place or not. As a guide, the effect of protease on the expression of the two reporter genes is illustrated below.

TABLE 1

Ratio of the expression of the genes in the presence and in the absence of FMDV L protease.

| Construct | neo | LacZ |
|---|---|---|
| pREV CG-50 | −51.85 | −5.53 |
| pREV CB-54 | −55.36 | +40.24 |
| pREV CB-55 | −34.65 | +84.42 |
| pREV CG-58 | −45.07 | +57.51 |
| pEMCV-D260-837 | −79.51 | +33.93 |

Example 2

Retroviral Vectors Comprising an REV-A IRES Sequence

A series of retroviral vectors were constructed using the REV-A sequences as IRES sites or as elements which increase encapsidation. FIG. 3 illustrates the vectors of the pREV HW series possessing MoMLV-type LTRs and the control vectors used in the experiments described below. Although they are not represented, vectors designated pMC which differ from pREV HW only in that their LTRs are of SNV origin, and negative controls in which the REV-A sequences are positioned in the opposite orientation (3'→5') relative to the LTRs, were also constructed. For all the molecular biology steps, these vectors are introduced into the plasmid pBR322.

1. Construction of the Retroviral Vectors

The control vector pEMCV-CBTV (pBC100) is a dicistronic vector comprising, in addition to the LTRs and the encapsidation region which are derived from MoMLV, the gene encoding placental alkaline phosphatase (plap) whose translation is cap-dependent and the neo gene whose translation is dependent on the EMCV IRES site (Torrent et al., 1996, Human Gene Therapy 7, 603–611).

The pREV HW vectors were obtained in the following manner:

REV HW-1: the REV-A fragment extending from nt 265 to 578 generated by PCR and digested with NheI is cloned between the plap and neo genes of pMLV-CB71 (Berlioz and Darlix, 1995, J. Virol. 69, 2214–2222).

pREV HW-2: the EcoRI fragment of pVL CBT5 (Torrent et al., 1996, Human Gene Therapy 7, 603–611) carrying the MoMLV 5' LTR and the encapsidation sequences of VL30 is introduced into the vector pREV HW-1 linearized with EcoRI.

pREV HW-3: the EcoRI fragment of pEMCV-CBTV containing the 5' LTR and the encapsidation sequences of MoMLV is inserted into the vector pREV HW-1 linearized with EcoRI.

pREV HW-4: the REV-A fragment extending from nt 452 to 578 generated by PCR and digested with NheI is cloned between the plap and neo genes of pMLV-CB71.

pREV HW-5: the EcoRI fragment of pVL CBT5 carrying the MoMLV 5' LTR and the encapsidation sequences of VL30 is introduced into the vector pREV HW-4 linearized with EcoRI.

pREV HW-6: the EcoRI fragment of pEMCV-CBTV containing the 5' LTR and the encapsidation sequences of MoMLV is inserted into the vector pREV HW-4 linearized with EcoRI.

The vectors of the pMC series are obtained according to the following construction scheme: the SNV LTRs are generated by PCR from the plasmid REV-A 2-20-6 (O'Rear and Temin, 1982, Proc. Natl. Acad. Sci. USA 79, 1230–1234; Darlix et al., 1992, J. Virol. 66, 7245–7252). The neo gene is isolated from pMLV-CB71 by digestion with SalI and BamHI and then introduced between the same sites of the vector pUC19 (Gibco BRL). The SNV 5' LTR (nt 1 to 861) is digested with HindIII and SalI, and inserted into pUC19-neo previously cleaved with these same enzymes. The SNV 3' LTR (nt 7230–8300) digested with SmaI and EcoRI is cloned into the preceding vector to give pCG-61 containing SNV 5' LTR-neo-SNV 3' LTR. In parallel, a vector designated pCG-62 is generated which differs from the preceding one by the deletion of the env sequences (nt 7230–7691) obtained by treatment with BglII-AvrII, Klenow and religation. The plap gene isolated from the Cla-12AP clone (DGoff) is introduced between the EcoRI and XbaI sites of a bluescript plasmid previously deleted for the SalI site (EcoRI-XhoI digestion) before being reisolated in the form of a KpnI-SalI fragment and cloned between the same sites of pCG-61 and pCG-62, to give pCG-63 and pCG-64 respectively. The LacZ gene is obtained by partial digestion of pREV CB-95 with the SalI and BamHI enzymes. Its insertion between the SalI and BamHI sites of pCG-61 and pCG-62 gives rise to pCG-65 and pCG-66 respectively. Finally, the LTR-Gene-LTR block is isolated from each plasmid pCG-62, pCG-64 and pCG-66 by HindIII-EcoRI digestion so as to be inserted into the vector pBR322 cleaved with these same enzymes. pMC1, pMC2 and pMC3 are generated.

2. Generation of Infectious Viral Particles and Determination of the Viral Titer and of the Expression of the Reporter Genes plap and neo The ecotropic complementation line GP+E-86 (Markowitz et al., 1988, J. Virol., 62, 1120–1124) and the NIH3T3 target cells (mouse fibroblast cells) available at ATCC are cultured at 37° C. in the presence of 5% $CO_2$ in DMEM medium (Dulbecco's Modified Eagle's Medium, Gibco BRL) supplemented with 10% newborn-calf serum. The GP+E-86 helper cells and the NIH3T3 target cells are cultured on the day before the transfection and infection. The viral infections are carried out according to the conventional protocol described in the literature.

20 µg of vectors pREV HW-1 to 6 as well as the reference vector pEMCV-CBTV are transfected in parallel into the GP+E-86 cells ($5 \times 10^5$ cells per 10-cm dish) according to the method of Chen and Okyama (1987, Mol. Cell. Biol., 7, 2745–2753; 1988, Bio/Techniques 6, 632–637). Various dilutions of stable or transient GP+E-86 culture supernatants are used to infect the NIH3T3 target cells inoculated the day before the infection at the rate of $2 \times 10^4$ cells per well. The viral supernatants were filtered beforehand (on 0.45 µm filters) and exposed to polybrene at a final concentration of 8 µg/ml. The infection is continued overnight at 37° C. and the next day, the cells are washed and cultured in fresh medium. After 48 h, the cells are placed in selective medium (1 mg/ml of G418) or stained in order to determine the number of cells expressing the plap alkaline phosphatase. Fixing is first carried out in a 1×PBS buffer containing 2% formaldehyde and 0.2% glutaraldehyde. After two rinses in 1×PBS followed by a 30-min incubation at 65° C. in 1×PBS, the cells are washed twice in AP buffer (0.1 M Tris-HCl pH 9.5, 0.1 M NaCl, 50 mM $MgCl_2$ in 1×PBS) and placed for 5 h in the staining solution (0.1 mg/ml of 5-bromo-4-chloro-3-indolyl phosphate (BCIP), 1 mg/ml of a nitroblue terazolium salt (NBT) and 1 mM Levamisol in AP buffer). These histochemical staining experiments confirm the expression of alkaline phosphatase in the GP+E-86 helper cells and in the NIH3T3 target cells.

The titer of the recombinant viruses is determined after transfection of the ecotropic GP+E-86 cells. After two days of incubation, the viral supernatant is harvested and used to determine the viral titer (transient expression). Next, the transfected cells are selected on G418 for one month. After this selection, the viral titer is determined on the harvested supernatant (stable expression). It corresponds to the number of infectious particles per ml of supernatant. Using the limiting dilution method, the NIH3T3 target cells are infected with serial dilutions of viral supernatant and, after two days of incubation, the cells are histochemically stained and counted.

The following results are obtained (Table 2):

| Vector | Transient expression (cfu/ml) | Stable expression (cfu/ml) |
|---|---|---|
| pREV HW-1 | — | — |
| pREV HW-2 | $0.2 \times 10^4$ | $3.2 \times 10^6$ |
| pREV HW-3 | $1.6 \times 10^4$ | $1.4 \times 10^9$ |
| pREV HW-4 | — | — |
| pREV HW-5 | $1.3 \times 10^4$ | $6.5 \times 10^5$ |
| pREV HW-6 | $2.0 \times 10^4$ | $4.5 \times 10^8$ |
| pEMCV-CBTV | $1.1 \times 10^4$ | $2.1 \times 10^8$ |

The vectors pREV HW-1 and pREV HW-4, lacking the conventional encapsidation region, are incapable of producing infectious viral particles after transfection into the MLV helper line (GP+E-86). However, it should be indicated that the pMC1 vector can be encapsidated into SNV virus particles after transfection of the SNV D17-C3A2 helper line (for example ATCC CRL8468), indicating that the REV-A sequences extending from nt 265 to 578 can be used in this context as encapsidation region. The retroviral vectors comprising both an REV-A sequence (265–578 or 452–578) and a conventional encapsidation region produce viral particles at a high titer (pREV HW-2, 3, 5 and 6). However, the association between the encapsidation region of MLV is found to be particularly advantageous since it gives viral titers 2 (pREV HW-6) to 5 times (pREV HW-3) as high as the reference vector pEMCV-CBTV combining this same encapsidation region and the EMCV IRES. Furthermore, comparison of the data obtained with the identical vectors varying only at the level of the REV-A segment used (pREV HW-2 and pREV HW-5 or pREV HW-3 and pREV HW-6) suggests that the sequence ranging from nt 265 to 578 is capable of cooperating with the encapsidation region as well as of enhancing the encapsidation of the viral RNAs and consequently of the viral titers. An element interacting positively with the encapsidation might be present between nt 452 and 265 in the REV-A genome.

3. Analysis of the Recombinant Viruses by Electron Microscopy

The morphology of the recombinant virions pREV HW produced after transfection of the GP+E-86 line with the corresponding vectors is analyzed by electron microscopy. The viruses obtained from pEMCV-CBTV under the same conditions and the wild-type retroviruses obtained after infection of the NIH3T3 cells with the FMLV-29 strain (Friend murine leukemia virus strain 29) are used as controls. The microscopy results indicate that the RNA content does not affect the morphology of the recombinant viruses.

4. Effect of Rapamycin on the Expression of the plap and neo Cistrons

The GP+E-86 cells are stably transfected with 20 μg of vectors of the pREV HW or pEMCV-CBTV series and cultured under selective conditions (G418) for 15 days. At 70 to 80% confluence, they are exposed to rapamycin at a final concentration of 20 ng/ml. The latter has an inhibitory effect on the cap-dependent translation varying from 15 to 40% according to the cell line (Beretta et al., 1996, EMBO J. 15, 658–664) but does not affect the cap-independent translation. The cellular extracts are prepared conventionally after 20 h of incubation. Briefly, the cells are washed twice in 1×PBS, placed in 1 ml of TEN (40 mM Tris-HCl pH 7.5, 1 mM EDTA, 50 mM NaCl) for a 10-cm dish and then recovered by scraping and centrifuged at low speed. The pellet is taken up in 100 μl of 0.25 M Tris-HCl, pH 8 and subjected to cell lysis using 3 freeze-thaw cycles. After centrifugation for 10 min at 14,000 g, the supernatant is recovered and may be stored at −70° C. until the enzymatic tests are carried out. The final protein concentration is determined by the Micro BCA test (Pierce). The plap enzymatic activity of the cellular extracts is evaluated spectrophotometrically (alkaline phosphatase kit, BIORAD). The plap units are determined relative to a standard consisting of calf intestinal alkaline phosphatase (Boehringer Mannheim). The neo activities are measured by the transfer of phosphate labeled with [$\gamma$-$^{32}$P] on neomycin (Ramesh and Osborne, 1991, Anal. Biochem. 193, 316–318). The results of the expression of the plap and neo genes measured in the absence and in the presence of rapamycin are illustrated in FIG. 4 and presented in Table 3.

TABLE 3

Effect of rapamycin on the expression of the plap and neo cistrons expressed as % relative to the nontreated cells.

| Cell line | Alkaline phosphatase | Neomycin phosphotransferase |
|---|---|---|
| GP + E-86 | — | — |
| pREV HW-1 | −40.9 | +21.5 |
| pREV HW-2 | +21.3 | +26.7 |
| pREV HW-3 | +34.8 | −6.5 |
| pREV HW-4 | −94.6 | +3.0 |
| pREV HW-5 | +66.7 | +46.9 |
| pREV HW-6 | +46.1 | +49.6 |
| pEMCV-CBTV | −2.6 | +20.5 |

In the vectors pREV HW-1 and pREV HW-4, the presence of rapamycin reduces the cap-dependent translation and increases that dependent on IRES. This stimulation can be expressed by a lower competition for the translational machinery in the presence of rapamycin. When two IRES elements are present, the addition of rapamycin is accompanied by an increase in the expression of the two genes. However, the quantitative expression data indicate that the relative activity of the IRESs is different, which suggests competition between them for the ribosomes.

In short, all the data show the presence of an effective IRES site in the 5' leader of the RNAs of the REV-A virus, and probably of an element interacting positively with the encapsidation. The minimum IRES element is contained within a sequence of 129 nt (positions 452 to 578).

Example 3

Transduction of Pluripotent Human Neuroectodermal Cells

This study is carried out in the human cell line Dev which constitutes a cellular model of the central nervous system, a potential target for human gene therapy. The Dev cells are derived from a human primary tumor of neuroectodermal origin (PNET) and behave like pluripotent stem cells (Derrington et al., 1997, Oncogene, in press). Furthermore, it is possible to induce their differentiation either into neurons or into glial cells (Derrington et al., 1997, supra; Dufay et al., 1994, Eur. J. Neurosci. 6, 1633–1640; Giraudon et al., 1993, Neurosci. 52, 1069–1079). In this study, the dicistronic vector pREV HW-3 (REV-A IRES 265–578) is compared with the control vector pEMCV CBTV (EMCV IRES).

The Dev cells are infected with a 1/100 dilution of viral supernatant for 2 days and then fixed, histochemically stained according to the protocol above and counted. The viral titer is similar for the two vectors and is of the order of $3\times10^3$ TU/ml. The transduction units (TU/ml) correspond to the ratio of the number of colonies×dilution of the infecting retrovirus to the total volume (ml) of the dilute vector placed over the cells.

The expression of the two neo and plap cistrons is also checked. To do this, the target cells are, as above, transduced with a 1/100 dilution of viral supernatant and selected in the presence of G418 for 3 weeks. The intensity of fluorescence is determined by flow cytometry with an antibody specific for plap (DAKO). It should be indicated that a polyclonal antibody is suitable. The results show the production of the plap enzyme by the cells transduced and selected on G418. In parallel, the synthesis of the plap enzyme is confirmed by histochemical staining of the resistant clones.

These data show that the dicistronic vector pREV HW-3 can efficiently transduce human cells derived from the central nervous system and transfer genes of interest into them, and confirm the functionality of the IRES REV-A site for mediating the production of the product of expression of the second cistron.

Moreover, various transduction protocols were studied for the purpose of optimization. The variants are the cell culture conditions in the presence or in the absence of serum and in the presence or in the absence of growth factors (FGF-2) and the production of the viruses in the presence or in the absence of serum. The following six protocols were compared with the pEMCV CBTV and pREV HW-3 viruses possessing the polytropic envelope GaLV (production on PG13 cells, ATCC CRL-10686).

Protocol 1: cells cultured in a medium with serum (10%), virus produced in the presence of serum (10%).

Protocol 2: cells cultured in a medium with serum (10%), virus produced in the absence of serum.

Protocol 3: cells cultured in a medium without serum, virus produced in the presence of serum (10%).

Protocol 4: cells cultured in a medium without serum, virus produced in the absence of serum.

Protocol 5: cells cultured in a medium without serum, virus produced in the presence of serum (10%), presence of FGF-2.

Protocol 6: cells cultured in a medium without serum, virus produced in the absence of serum, presence of FGF-2.

The percentage of Dev cells transduced is determined by flow cytometry (FIG. 5). The percentage of cells transduced by pREV HW-3 exceeds 30% when the culture of the Dev cells is carried out in the absence of serum. Such a % is not reached with the conventional pEMCV CBTV virus. The addition of growth factors is also advantageous. Among all the protocols used, protocol 5 makes it possible to transduce more than 50% of Dev cells. These results show that the polycistronic vectors of the invention carrying the REV-A IRES are functional for transducing the pluripotent neuroectodermal cells. The development of protocols for the efficient transduction of human cell lines is an essential point in the development of gene transfer strategies.

The expression of the plap and neo cistrons is evaluated after neuronal and glial differentiation (Derrington et al., 1997, supra). Briefly, the Dev cells adopt a differentiated phenotype in the presence of serum and of FGF-2 whereas when the culture is carried out in the absence of serum, the phenotype is pluripotent. The immunofluorescence results with an anti-plap specific antibody on Dev cells transduced, selected on G418 and differentiated, show expression of plap in the neuronal and glial cells. These data suggest that the differentiation state does not inhibit the translation mediated by the REV-A IRES.

What is claimed is:

1. A vector for the expression of one or more genes of interest comprising a nucleotide sequence isolated from the 5' end of the genomic RNA of a an avian reticuloendotheliosis virus of type A (REV-A), wherein said nucleotide sequence comprises at least the portion of the sequence presented in SEQ ID NO: 2 starting at nucleotide 452 and ending at nucleotide 578 or the DNA equivalent of said portion in which U nucleotides are replaced by T nucleotides.

2. The vector according to claim 1, wherein said vector is a plasmid vector or a viral vector selected from the group consisting of a poxviral vector, an adenoviral vector, a baculoviral vector, a herpesviral vector, an adeno-associated viral vector and a retroviral vector.

3. The vector according to claim 1, which is a retroviral vector and which comprises at least the following elements associated in a functional manner: a retroviral 5' LTR and a retroviral 3' LTR, one or more genes of interest, and said nucleotide sequence to allow the encapsidation of said vector into a viral particle or as an IRES site to allow or promote the expression of a gene of interest positioned downstream of said nucleotide sequence.

4. The retroviral vector according to claim 3, in which said nucleotide sequence is an IRES site and comprising, in addition, an encapsidation region which is heterologous to said nucleotide sequence.

5. The retroviral vector according to claim 3, comprising at least the following elements (a) to (f) associated in a functional manner:
   (a) a retroviral 5' LTR,
   (b) an encapsidation region,
   (c) a first gene of interest,
   (d) an IRES site,
   (e) a second gene of interest, and
   (f) a retroviral 3' LTR,
wherein at least one of the encapsidation region and the IRES site consists of said nucleotide sequence.

6. The retroviral vector according to claim 3, wherein said vector comprises the following elements (a) to (h) associated in a functional manner:
   a) a retroviral 5' LTR,
   b) an encapsidation region,
   c) a first gene of interest,
   d) an internal promoter region of a different origin from that of said retroviral 5' LTR,
   e) a second gene of interest,
   f) an IRES site,
   g) a third gene of interest, and
   h) a retroviral 3' LTR,
wherein at least one of the encapsidation region and the IRES site consists of said nucleotide sequence.

7. The retroviral vector according to claim 6, in which the internal promoter region, the second gene of interest, the IRES site and the third gene of interest are in an opposite orientation relative to the retroviral 5' and 3' LTRs.

8. The retroviral vector according to claim 5, in which the encapsidation region is obtained from a murine retrovirus, or from a VL30-type retrotransposon and the IRES site comprises the portion of the sequence presented in the sequence identifier SEQ ID NO:2:
   (i) starting at nucleotide 1 and ending at nucleotide 578, or
   (ii) starting at nucleotide 265 and ending at nucleotide 578,
   or to the DNA equivalent of said portion (i), or (ii), in which U nucleotides are replaced by T nucleotides.

9. The retroviral vector according to claim 8, in which the encapsidation region is obtained from an MoMLV and the IRES site comprises the portion of the sequence presented in sequence identified SEQ ID NO:2 starting at nucleotide 265 and ending at nucleotide 578, or the DNA equivalent of said portion in which U nucleotides are replaced by T nucleotides.

10. The vector according to claim 1, comprising a gene of interest encoding a product of expression selected from factor VIII, factor IX, the CFTR protein, dystrophin, insulin, alpha-, beta- or gamma-interferon, an interleukin (IL) and a selectable marker.

11. The vector of claim 1, wherein said nucleotide sequence comprises the portion of the sequence presented in the sequence identifier SEQ ID NO:2:
   (i) starting at nucleotide 1 and ending at nucleotide 578, or
   (ii) starting at nucleotide 265 and ending at nucleotide 578,
   or to the DNA equivalent of said portion (i), or (ii), in which U nucleotides are replaced by T nucleotides.

12. The retroviral vector according to claim 4, in which said encapsidation region is from MoMLV.

13. A viral particle generated from the vector according to claim 1.

14. An isolated cell comprising the vector according to claim 1 or infected with the viral particle according to claim 13.

15. A method for providing an internal ribosome entry site (IRES) to a vector for the transfer and expression of one or more genes of interest, comprising the step of introducing into said vector a nucleotide sequence isolated from the 5' end of the genomic RNA of an avian reticuloendotheliosis virus of type A (REV-A) wherein said nucleotide sequence comprises at least the portion of the sequence presented in SEQ ID NO: 2 starting at nucleotide 452 and ending at nucleotide 578 or the DNA equivalent of said portion in which U nucleotides are replaced by T nucleotides.

16. The method of claim 15, wherein said nucleotide sequence comprises the portion of the sequence presented in the sequence identifier SEQ ID NO:2:

(i) starting at nucleotide 1 and ending at nucleotide 578, or (ii) starting at nucleotide 265 and ending at nucleotide 578, or to the DNA equivalent of said portion (i), or (ii), in which U nucleotides are replaced by T nucleotides.

17. A method of allowing or activating the encapsidation of a retrovirus or of a retroviral vector, comprising the step of introducing into said retrovirus or retroviral vector, a nucleotide sequence isolated from the 5' end of the genomic RNA of a reticuloendotheliosis virus of type A (REV-A), wherein said nucleotide sequence comprises at least the portion of the sequence presented in SEQ ID NO: 2 starting at nucleotide 265 and ending at nucleotide 578 or the DNA equivalent of said portion in which U nucleotides are replaced by T nucleotides.

18. The method of claim 17, wherein said nucleotide sequence comprises the portion of the sequence presented in the sequence identifier SEQ ID NO:2:

(i) starting at nucleotide 1 and ending at nucleotide 578, or to the DNA equivalent of said portion (i), in which U nucleotides are replaced by T nucleotides.

19. A method for the preparation of one or more polypeptides of interest by recombinant techniques, comprising the step of culturing in vitro a cell comprising the vector according to claim 1 and harvesting said polypeptide(s) from the supernatant or from the cell culture.

20. An in vitro method for expressing one or more genes of interest into pluripotent cells, comprising the step of transfecting or infecting said pluripotent cells with the vector according to claim 1 or the viral particle according to claim 13.

21. The method of claim 20, wherein said pluripotent cells are of the central nervous system.

22. A method for the preparation of one or more polypeptides of interest by recombinant techniques, comprising the step of culturing in vitro a cell infected with the viral particle according to claim 13 and harvesting said polypeptide(s) from the supernatant or from the cell culture.

* * * * *